US009504512B2

(12) United States Patent
Poulsen

(10) Patent No.: US 9,504,512 B2
(45) Date of Patent: Nov. 29, 2016

(54) ELECTROSURGICAL INSTRUMENT

(75) Inventor: Henrik Bisgaard Poulsen, Slangerup (DK)

(73) Assignee: LINA MEDICAL APS, Glostrup (DK)

( * ) Notice: Subject to any disclaimer, the term of this patent is extended or adjusted under 35 U.S.C. 154(b) by 126 days.

(21) Appl. No.: 14/129,902

(22) PCT Filed: Jun. 28, 2012

(86) PCT No.: PCT/EP2012/062560
§ 371 (c)(1),
(2), (4) Date: Dec. 27, 2013

(87) PCT Pub. No.: WO2013/001000
PCT Pub. Date: Jan. 3, 2013

(65) Prior Publication Data
US 2014/0142567 A1    May 22, 2014

(30) Foreign Application Priority Data
Jun. 28, 2011    (EP) ..................... 11171767

(51) Int. Cl.
*A61B 18/12*    (2006.01)
*A61B 18/08*    (2006.01)
(Continued)

(52) U.S. Cl.
CPC ............. *A61B 18/085* (2013.01); *A61B 18/10* (2013.01); *A61B 18/1233* (2013.01); *A61B 18/14* (2013.01); *A61B 18/1402* (2013.01); *A61B 18/1442* (2013.01); *A61B 2018/0013* (2013.01); *A61B 2018/00559* (2013.01); *A61B 2018/00589* (2013.01); *A61B 2018/00601* (2013.01); *A61B 2018/00642* (2013.01); *A61B 2018/00708* (2013.01); *A61B 2018/00755* (2013.01); *A61B 2018/00875* (2013.01);
(Continued)

(58) Field of Classification Search
CPC  A61B 18/085; A61B 18/10; A61B 18/1233; A61B 18/14; A61B 18/1402; A61B 18/1442; A61B 2018/0013; A61B 2018/00559; A61B 2018/00589; A61B 2018/00601; A61B 2018/00642; A61B 2018/00708; A61B 2018/00755; A61B 2018/00875; A61B 2018/126; A61B 2018/1286; A61B 2018/1407; A61B 2018/1412
See application file for complete search history.

(56) References Cited

U.S. PATENT DOCUMENTS

| 4,196,734 A |   | 4/1980 | Harris |
|---|---|---|---|
| 4,493,320 A | * | 1/1985 | Treat .............................. 606/47 |

(Continued)

FOREIGN PATENT DOCUMENTS

| EP | 1 527 743 A2 | 5/2005 |
|---|---|---|
| EP | 1 089 664 B1 | 9/2005 |

(Continued)

*Primary Examiner* — Daniel Fowler
(74) *Attorney, Agent, or Firm* — Muncy, Geissler, Olds & Lowe, P.C.

(57) ABSTRACT

An electrosurgical instrument and apparatus for use with the instrument
A bipolar electrosurgical instrument for use with an electrosurgical generator. The bipolar electrosurgical instrument incorporates a transformer having an input side or end electrically connected to the electrosurgical generator and an output side or end electrically connected to said bipolar electrosurgical instrument. The inexpensive bipolar electrosurgical instrument can be used with most conventional bipolar electrosurgical generators as well as with bipolar electrosurgical generators specifically designed for use with said instrument.

1 Claim, 5 Drawing Sheets

(51) Int. Cl.
*A61B 18/14* (2006.01)
*A61B 18/10* (2006.01)
*A61B 18/00* (2006.01)

(52) U.S. Cl.
CPC . *A61B 2018/126* (2013.01); *A61B 2018/1286* (2013.01); *A61B 2018/1407* (2013.01); *A61B 2018/1412* (2013.01)

(56) References Cited

U.S. PATENT DOCUMENTS

| | | | |
|---|---|---|---|
| 4,955,377 A * | 9/1990 | Lennox et al. | 607/105 |
| 5,269,780 A * | 12/1993 | Roos | 606/42 |
| 5,376,094 A * | 12/1994 | Kline | 606/113 |
| 5,445,635 A | 8/1995 | Denen et al. | |
| 6,267,759 B1 * | 7/2001 | Quick | 606/47 |
| 2004/0181219 A1 | 9/2004 | Goble et al. | |
| 2005/0096681 A1 | 5/2005 | Desinger et al. | |
| 2005/0234442 A1 * | 10/2005 | Spears | 606/39 |
| 2006/0116675 A1 * | 6/2006 | McClurken et al. | 606/51 |

FOREIGN PATENT DOCUMENTS

| | | |
|---|---|---|
| EP | 1 150 616 B1 | 9/2005 |
| EP | 2210567 A1 | 7/2010 |
| WO | WO 2008/010150 A2 | 1/2008 |

* cited by examiner

ELECTROSURGICAL INSTRUMENT

INTRODUCTION

The present invention relates to a handheld electrosurgical instrument for use with an electrosurgical generator and to a method of powering electrosurgical instruments by use of a common electrosurgical generator. The electrosurgical instrument to which the invention relates comprises a connector for connection to an electrosurgical generator, electrode means e.g. for cutting or cauterization, and a handle for manipulating the electrodes.

BACKGROUND OF THE INVENTION

Electrosurgery is the application of a high-frequency electric current to biological tissue as a means to cut, coagulate, desiccate, or fulgurate tissue. It enables precise cuts with limited blood loss due to a combined cutting and coagulation procedure. Electrosurgical devices are therefore frequently used during surgical operations helping to prevent blood loss in hospital operating rooms.

In electrosurgical procedures, the tissue is heated by an electric current in the tissue. The current is created by a high frequency generator, in particular a radio frequency generator to which the electrosurgical instrument is connected.

Electrosurgical instruments exist in different shapes and for different purposes. Examples are forceps, loop electrodes, scissors, pencils, scalpels etc.

Electrosurgical instruments can be classified in at least two different groups, namely monopolar instruments and bipolar instruments. The monopolar instruments works by transmitting a current from an electrode which is manipulated by a handle to an electrode which is attached to the body of the patient, typically adhesively attached. Within the context of the present application the term "bipolar electrosurgical instrument" is to be understood as an electrosurgical instrument where both electrodes are manipulated by the handle and therefore both forms part of the handheld part of the electrosurgical instrument itself. The flow of electricity is substantially confined to the space between the opposite electrode faces of the electrosurgical instrument, such as e.g. bipolar forceps or bipolar loop electrodes, so that tissue damage is substantially confined to tissue situated between said electrodes. Since no dispersive electrode is required remote from the patient, less electrical current is needed to obtain the same effects than when using monopolar electrosurgical instruments, where the current must pass through the body to get to the dispersive electrode.

Within the context of the present application the term "bipolar electrosurgical generator" is synonymous with a high frequency generator, in particular a radio frequency generator, for use with a bipolar electrosurgical instrument. A "bipolar electrosurgical generator" may thus also be a multipurpose electrosurgical generator with both monopolar and bipolar functions. Within the context of the present application bipolar or monopolar electrosurgical generators and bipolar or monopolar electrosurgical instruments can be used.

Before surgery the surgeon will have to select a power output level which is suitable for the instrument which is used. Depending on the generator which is used, the surgeon may have to live with the voltage amplitude level, or the surgeon may have to adjust the voltage amplitude level as part of the adjustment procedure. The setting may typically be based on guidelines made by the provider, as well as other indications such as previous experiences and other kinds of safety regulations. During the surgical procedure, in particular when operating on thick or large tissue objects, such as the cervix or uterus, the surgeon may benefit from increased voltage level in order to overcome the resistance through the actual tissue. Under other circumstances the surgeon may need to lower a presumed too high voltage level. Until now the solution for obtaining increased or lowered voltage is to use an appropriate electrosurgical generator and/or to amend the settings on the generator. This may, however, be inconvenient, not least if the generator is subsequently or mainly to be used with another setting. In worst case, the practitioner who subsequently uses the generator with another instrument may forget to set back the changed settings. Further, it may generally be disturbing for the surgeon having to remember to adjust the settings depending on the instrument which is being used, and the availability of different instruments requiring different settings in one operating room may be a cause of confusion and potential errors.

Generally, there is a need to develop cost-saving electrosurgical techniques and instruments towards eliminating unintended effects and limitations related to their uses.

SUMMARY OF THE INVENTION

It is an object of embodiments of the invention to provide an electrosurgical instrument as an alternative and/or supplement to known bipolar electrosurgical instrument, in particular when operating on thick tissue objects.

It is a further object to provide a bipolar electrosurgical instrument that enables the surgeon to operate at voltage levels different from the levels defined by the associated electrosurgical generator.

It is a further object of the invention to provide a bipolar electrosurgical instrument for stepping up voltage output level beyond maximum factory setting of the bipolar surgical generator.

It is a further object of the invention to provide an inexpensive bipolar electrosurgical instrument.

It is a further object of the invention to provide a bipolar electrosurgical instrument that is more user friendly than known instruments.

It is a further object of the invention to provide a bipolar electrosurgical instrument with coated electrodes that perform better than known instruments with coated electrodes, in particular with Teflon™ coated electrodes.

According to these and other objects, the present invention, in a first aspect, provides a handheld electrosurgical instrument which incorporates a transformer having an input electrically connected to the connector and an output electrically connected to the electrode means, the transformer being adapted to change voltage of an electrical signal from the generator, particularly to increase the voltage such that the voltage of the signal which is received by the electrode means is higher than the voltage of the signal which is transmitted from the generator.

In a second aspect, the invention provides a method for providing a desired voltage between electrodes of an instrument, the method comprising providing a generator which generates a first electrical signal with a first voltage, and transforming the first electrical signal into a second electrical signal with a second voltage which is different from the first voltage, and providing the second electrical signal to the electrodes.

In a third aspect, the invention provides a method of powering different handheld electrosurgical instruments which require different voltage amplitude, the method comprising: providing a single electrosurgical generator; providing at least two different handheld electrosurgical instruments each having electrode means for cutting or cauterization and requiring different voltage from the electrosurgical generator, characterized in that both electrosurgical instruments are connected to receive identical electrical signals from the electrosurgical generator, and the electrical signal for at least one of the handheld electrosurgical instruments is changed by use of a transformer connected between the electrosurgical generator and the electrode means of one of the electrosurgical instruments.

Accordingly, the invention allows connection of the instrument to a generator which is also used for other purposes requiring a different voltage, and the surgeon does not have to change settings on the generator since the instrument itself includes a transformer for amending the signal after it is received from the generator.

The generator may remain in a setting for a different type of instrument. In fact, the generator may be tailored specifically for a completely different kind of instrument. By way of example, the generator may be tailored for a bipolar scissor/forceps type cutter cutting device. Such a device typically cuts through relatively thin layers of tissue, and the required voltage level is relatively low. According to this invention, a bipolar instrument of the wire loop type for cutting tissue may include a transformer such that it can be connected to the mentioned generator. The transformer may step up the delivered voltage such that the loop becomes capable of performing cuts irrespective of the larger tissue thicknesses and thus increased need for voltage which is typical for loop-type cutters. Conventional electrosurgical generators can be utilized with the instrument according to the present invention.

The electrosurgical generator may be configured to operate in e.g. cut mode, blend mode, and/or coagulation mode, e.g. using the electrosurgical instruments disclosed in the applicants own international patent application no. WO 2008/010150, and European patent applications no. EP 1 089 664 and EP 1 150 616.

The transformer can optionally be integrated in the electrosurgical instrument in a manner that allows it to be switched on or off during surgery. Transformers of different sizes and capacity can be integrated in an electrosurgical instrument; so the electrosurgical instrument according to the present invention is tailored to broader and more versatile purposes and uses than conventional electrosurgical instrument without transformers.

The transformer can be a toroidal transformer having a toroidal shaped core. The transformer can also have any circumferential or polygonal shape having a core with any circumferential or polygonal shape. A toroidal transformer is suitable when placed in a cylindrical handle. The core can also have the form of a rod, like a cylinder with the primary and secondary windings winded coaxially but may be separated from each other. The core can be a laminated core, an iron core, a ferrite core or the core can consist of air. Advantageously, the transformer can have the same shape as the handle and thus be used directly for manipulating the instrument during surgery.

The input side or input end and the output side or output end of the transformer are the primary and secondary parts of the transformer, respectively. In a dual winding transformer, the primary winding is the input side or input end of the transformer and the secondary winding is the output side or output end. In an autotransformer some of the winding is used both for the primary and the secondary side. The input side of the autotransformer is the side or end where the electrical wires to the primary side are and the output side of the autotransformer is the side or end where the electrical wires to the secondary side are.

The input side or input end of the transformer of the electrically instrument can e.g. be electrically connected to the electrosurgical generator by wires and plugs, e.g. a power cable with a euro connector.

The transformer may comprise adjustment means enabling the user to adjust the ratio between voltage of the electrical signal from the generator and voltage of the electrical signal to the electrode means.

The transformer could be a piezo-transformer, an electronic switch-mode transformer, or a traditional transformer with a core, a primary coil having a first number of windings, and a secondary coil with a second number of windings that is higher than the first number of windings. Voltage can be applied to the primary coil and a current flows and drives magnetic flux through the core. Energy can then be transferred from the primary coil to the secondary coil, thus inducing a secondary voltage in the secondary coil amplified as defined by the ratio between the number of second and first windings. The core can be a laminated core, an iron core, a ferrite core, or the core can consist of air.

A voltage step-up appropriate for electrosurgical procedures can be envisaged if the second number of windings is at least greater than the primary number of windings, e.g. between 1.1 and 1.9, such as between 1.2 and 1.6 such as between 1.3 and 1.5 times the first number of windings and more preferred at least 1.5 times the first number of windings. The second number of windings can also be at least twice the first number of windings.

In an expedient embodiment according to the present invention, which is particularly useful at radio frequencies, the core can be ferromagnetic, (ferritic), whereby only a small externally imposed magnetic field can cause the core material to be magnetized. Ferromagnetic materials are easily magnetized; such materials include but are not limited to materials such as iron, cobalt, nickel, and alloys or compounds containing such elements.

Different kinds of electrosurgical instruments may require different voltage levels to perform the best for a given patient in a given surgical procedure. Instead of using a customized expensive electrosurgical generator for each and every brand of surgical instrument the novel modified electrosurgical instrument incorporating a transformer according to the present invention can be used. The modified electrosurgical instrument is simple and fast to operate and makes a conventional electrosurgical generator which can operate at higher voltage levels than declared, thus suddenly making said conventional electrosurgical generator multifunctional and versatile.

Step-down transformers incorporated in an electrosurgical instrument are also foreseen within the scope of the present invention in case the conventional electrosurgical generator only allows application of a too high voltage.

A very convenient design of the electrosurgical instrument according to the present invention includes a transformer in the form of a bar-type transformer or a toroidal transformer. Such an elongated element or circular element has a shape fitting perfect inside a part of a housing or the casing of an electrosurgical instrument and is easy to operate when held in the hand. The core and windings of the transformer can conveniently be shielded and protected from the surroundings if the transformer is placed inside a part of the housing or the casing of the electrosurgical instrument, e.g. inside the handle or inside a part of the handle.

A traditional transformer with two separate coils provides an additional advantage of providing galvanic isolation between the generator and the electrode means, i.e. there are no metallic conduction path there between. The electrode means are not necessarily dependent on galvanic isolation, and, on the contrary, the transformer may be adapted to provide a metallic conduction path between the generator and the electrode means.

The transformer can e.g. be an autotransformer to minimise size, weight and production costs and further to provide the mentioned metallic conduction path. The autotransformer can be the bar-type autotransformer or the toroidal autotransformer or can have any other shape.

The electrosurgical instrument may have a lot of different means that improves user-friendliness, including but not limited to, means for monitoring transformation ratio, e.g. a display, means for on/off shifting transformer, means for monitoring voltage level, means for monitoring amperage, and any other means for displaying parameters associated with the energy application and use of the electrosurgical instrument prior to, during and subsequent to the surgical procedure. Preferably such means can be accessed via or at a part of the instrument's housing or casing, e.g. the handle.

A suitable shape and size of a transformer to be incorporated in an electrosurgical instrument is a bar-type transformer. Such a transformer is substantially cylindrical, optionally having an exterior diameter of between 0.5-4 cm, preferably about 1 cm, and a length of between 5 and 20 cm. The transformer can also be substantially toroidal optionally having an exterior diameter of less than 4 cm, preferably less than 2 cm, and a length of between 0.5 cm and 2 cm, preferably between 0.75 cm and 1 cm. These intervals define appropriate dimensions for a transformer to be incorporated in the electrosurgical instrument according to the present invention without adding or only adding insignificant volume or length to said electrosurgical instrument. Thus the electrosurgical instrument fits well in the hand of the surgeon, who can easily manoeuvre and operate the instrument. The exterior surface of at least a part of the electrosurgical instrument, e.g. a part of the housing or casing, may also have tactile means to further improve gripping properties.

To save space the toroidal transformer can preferably be positioned in the handle with the length axis of the toroidal transformer collinear with the length axis of the handle.

Contemplated electrosurgical instruments according to the present invention include but are not limited to electrosurgical instruments configured to provide at least one of the functions cut, coagulate, and ablate. In particular the electrosurgical instrument can be a bipolar forceps, bipolar loop electrode, bipolar scissors, bipolar pencil, bipolar scalpel, or a bipolar electrosurgical instrument incorporating and combining one or more functions thereof. The electrosurgical instrument can also be a monopolar pencil or scalpel. Optionally at least one of the electrodes of the bipolar electrosurgical instrument has an area provided with a non-stick coating.

The electrosurgical instrument can be of the kind having a bipolar loop electrode. Particularly, the invention may enable such an instrument to be powered by a generator which is supposed to power a bipolar forceps type instrument where the distance between the electrodes is much lower than the distance between the two loop-forming electrodes. Accordingly, the invention enables an easy switching between the use of a forceps type instrument and a loop-type instrument.

The loop can comprise a first wire part and a second wire part ending into an insulating holding member, where the insulating holding member can hold the first and the second wire parts together in a loop-shape. Optionally the first and the second wire parts each can have a knot for securing inside one or more cavities in the insulating holding member.

The first and the second wire parts are connected to the electrical wires from the transformer. The current from the electrosurgical generator can be driven through a first circuit established by the first wire part, the tissue to be treated and the second wire part.

It is advantageous that the holding member comprises two cavities for receiving respective knots. Each cavity has an entrance channel and an exit channel. The entrance channel can have a diameter that is equal to or larger than the diameter of the knot so as to allow the knot to be received in the cavity. The exit channel may have a diameter that is smaller than the diameter of the knot so that the knot cannot be introduced into the exit channel. The entrance channel and the exit channel may be one tapering channel. The knot can be made of a hard material or, as mentioned above, just be tied on a first end of the first and the second wire parts. The cavity can constitute the entrance channel. Alternatively, the knot can be made of a flexible material and in that case the diameter of the entrance channel can be slightly smaller than the diameter of the knot to ensure firm securing.

The wire part with the knot at the one first end can be introduced into and through the entrance channel and then through the exit channel with the end without the knot first. The wire part will not be able to be introduced further than until the knot hits the exit channel where the entrance and the exit channels meet. When the wire part is introduced so far the end without the knot will stick out from the holding member at the other end of the exit channel. The wire part can be bent manually just outside the holding member, which will fix the position of the wire part. This can also be done with the other wire part through the other entrance and exit channels.

Where the entrance channel meets the exit channel the entrance channel can have an increased diameter like a spherical cavity. The advantage of the spherical cavity is that the knot will be prevented to as easily fall back through the entrance channel.

The ends of the wire parts sticking out of the holding member can be welded or in any other way attached to electric conductors from the transformer.

In a preferred embodiment the transformer can be incorporated inside a part of a housing or a casing of the electrosurgical instrument, preferably inside a handle or part of a handle of the electrosurgical instrument.

Since the transformer can be made so small that the transformer easily can be incorporated inside the electrosurgical instrument the addition of the transformer will not make the electrosurgical instrument in any way less handy and less easy to use.

In an advantageous embodiment the electrosurgical instrument can have a circuit controlling a switching of the electrosurgical instrument between a measurement mode and an operating mode.

The circuit can comprise switches to switch the electrosurgical instrument between the measurement mode and the operating mode.

In the measurement mode a measurement unit can apply a voltage over electrodes, measure the current through the tissue between the electrodes and in electrical contact with the electrodes and calculate the impedance of the tissue. If the calculated impedance is above a certain pre-set value the electrodes are assumed not to be in contact with the tissue and the timer will not send a signal to switch the electrosurgical instrument over to the operating mode. The electrodes can be the bipolar forceps, the bipolar loop electrode, the bipolar scissors, the bipolar pencil, the bipolar scalpel, or the bipolar electrosurgical instrument incorporating and combining one or more functions thereof.

A situation where a high voltage is applied over the electrodes without the electrodes being in contact with anything means a danger that the electrodes by accident touches and destroys tissue, that should not be cut, coagulated or removed. Since the electrosurgical instrument according to the present invention is not switched over to the operating mode, when the impedance is too high, that danger is eliminated.

When the measurement unit in the measurement mode registers that the impedance is zero or nearly zero (below another preset value) the timer will be stopped to switch over the electrosurgical instrument to the operating mode. In this way the electrodes will not be destroyed by overheating, as well as very hot elements also can be a danger for surrounding tissue.

In another embodiment the electrodes in the measurement mode can be identical to the electrodes in the operating mode.

In a favorable embodiment, the circuit can comprise a timer that periodically controls the switching of the electrosurgical instrument between the measurement mode and the operating mode with a period that is less than 5 sec. long, preferably less than 1 sec. long, more preferably less than 300 msec. long, even more preferably less than 100 msec. long, yet more preferably less than 30 msec. long, yet even more preferably less than 10 msec. long, further more preferably less than 3 msec. long, even further more preferably less than 1 msec. long, yet further more preferably less than 300 μsec. long, yet even further more preferably less than 100 μsec. long and most preferably less than 30 μsec. long.

The shorter the period is, the smaller is also the energy driven through the electrodes and the tissue during one operating mode will be. If something goes wrong during the operating mode, using the short period only little energy will be delivered to the tissue before the electrosurgical instrument is switched to the measurement mode and the fault can be detected if the fault is due to too low or too high impedance. With a shorter period there is a much smaller risk that the electrosurgical instrument will cause any unwanted injury to the tissue.

Using the short period the energy driven through the electrodes and the tissue will be very small after the measurement unit has measured that the impedance is above a preset value or below another preset value. By using a short period the electrosurgical instrument will very fast stay in the measurement mode.

In yet another embodiment the circuit can comprise at least one switch controlled by the circuit, where in the measurement mode the generator is disconnected from the electrodes by the at least one switch.

The generator can be disconnected from the measurement unit and from the electrodes during measurement of current through the electrodes and through the tissue between the electrodes when a voltage is applied over the electrodes by e.g. the measurement unit. The advantage of disconnecting the generator in this case is that the measurement unit does not need to be built for high voltage but only for low voltage, which will make the construction of the measurement unit much cheaper. The electrodes can be the bipolar forceps, the bipolar loop electrode, the bipolar scissors, the bipolar pencil, the bipolar scalpel, or the bipolar electrosurgical instrument incorporating and combining one or more functions thereof.

The invention also relates to an electrosurgical apparatus comprising the electrosurgical instrument defined above and an electrosurgical generator for powering the instrument.

DETAILED DESCRIPTION OF AN EMBODIMENT

The invention will be described in further details below with reference to the accompanying drawing illustrating as an example a bar-type transformer incorporated in a bipolar electrosurgical loop electrode instrument.

Figures 1, 2A:
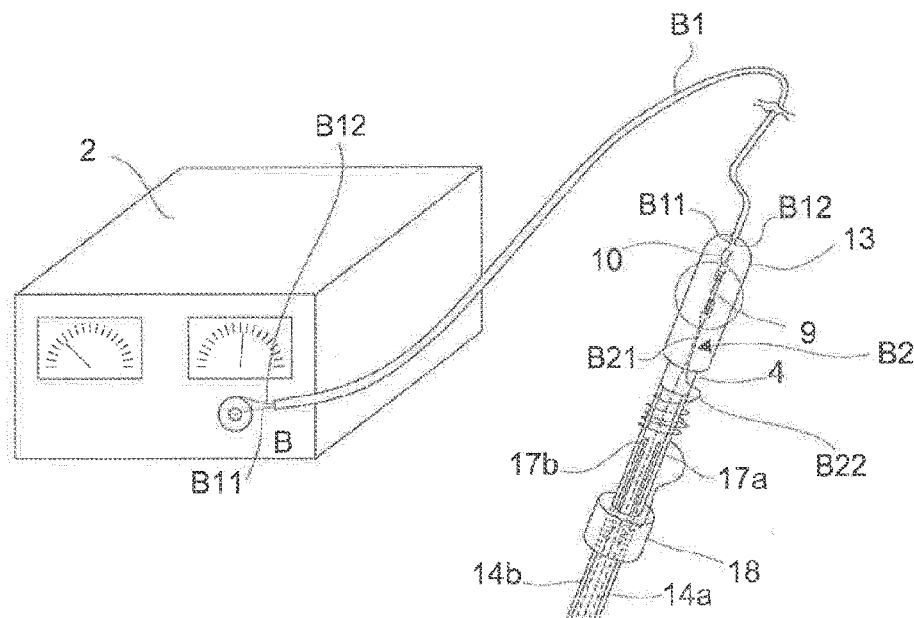
FIG. 1 illustrates, in a perspective principle sketch, a bipolar electrosurgical loop instrument coupled to an electrosurgical generator.
FIG. 2a illustrates, in an enlarged scale perspective fragmentary view, the transformer of the bipolar electrosurgical loop instrument shown in FIG. 1, which transformer is a bar-type core with a primary coil and a secondary coil.

In the figures a bipolar electrosurgical generator is, as a non-limiting example, shown with the bipolar electrosurgical instrument according to European patent application no. EP09151319 modified with a transformer according to the invention and further modified as shown in FIG. 1. The proportions between transformer, bipolar electrosurgical instrument and bipolar electrosurgical generator are not to be taken for real, said proportions are used to better illustrate the components of the bipolar electrosurgical devices according to the present invention.

FIG. 1 shows, in perspective, a general view of a bipolar electrosurgical instrument 1 connected to a bipolar electrosurgical generator 2. The bipolar electrosurgical instrument 1 has a hollow shaft 3 with a proximal end 4 and a distal end 5. The hollow shaft 3 is defined at least by an outer tubular casing 6 inside which an inner tubular casing 7 extends reciprocatingly. An output B of the bipolar electrosurgical generator 2 providing alternating current is connected to a primary coil 8 of a transformer 9 via electric wire B1 with electric conductors B11 and B12. In FIG. 1 the electric wire B1 is for illustrative purposes shown fragmented by fragment lines B1a.

In one or both of the electric conductors B11 and B12 an actuation knob 10 connects and disconnects the bipolar electrosurgical generator 2 from the primary coil 8 of the transformer 9. A secondary coil 11 of the transformer 9 has two ends in the form of two electric conductors B21 and B22 forming an electric wire B2. The secondary coil 11 is connected to a loop electrode 12, such as an electrically conductive resilient looped wire part, via the electric conductors B21. The loop electrode has an electrically isolating layer 12a except at the tip 12b, where the loop electrode is bare. Four electric electrode wires 14a,14b of which only two are visual in FIG. 1, extend slidingly lengthwise in the circumferential space between the inner tubular casing 7 and the outer tubular casing 6 in recesses in one or more spacer plugs 15, of which only one can be seen in FIG. 1. Each electric electrode wire 14a,14b has a distal end configured as a flat conductive plate or blade 16a,16b,16c,16d of enlarged surface area to establish good contact with an object (not shown) to be cut. The electric electrode wires 14a,14b are isolated from the loop electrode 12. The electric electrode wires 14a,14b have proximal ends connected to the electric conductor B22. The bipolar electrosurgical generator 2 supplies the loop electrode 12 and the four flat conductive plates or blades 16a,16b,16c,16d via the transformer 9 with electrical power to enable electrosurgical cutting or coagulating between the loop electrode 12 and the four flat conductive plates or blades 16a,16b,16c,16d.

The inner tubular casing 7 accommodates, as indicated by dashed line, the loop electrode 12. The actuation knob 10 is situated on a first handle 13 at the proximal end of the inner tubular casing 7. The actuation knob 10 enables the surgeon to switch cutting or coagulating current through the loop electrode 12, then through an object (not shown) and finally through the four flat conductive plates or blades 16a,16b, 16c,16d on and off on demand to enable electrosurgical cutting or coagulating and according to the surgeons choice only by a simple pressure on the actuation knob 10. The first handle 13, that incorporates the transformer 9, is also used for reciprocating the loop electrode 12.

The outer tubular casing 6 has at its proximal end 4 a number of longitudinal slide grooves 17a,17b of which only two can be seen in FIG. 1. The number of slide grooves 17a,17b corresponds to the number of electric electrode wires 14a,14b. The proximal ends of the electric electrode wires 14a,14b are passed through the corresponding slide grooves 17a,17b and secured to a second handle 18 for reciprocating, said blade electrodes 16a,16b,16c,16d in and out of the distal end 5 of the hollow shaft 3 as occasion requires.

In the exemplary bipolar electrosurgical instrument 1, the step-up voltage transformer 9, which is shown in the principle sketch of enlarged scale view of FIG. 2a, is integrated in the first handle 13 and electrically inserted between the electric wires B1 and B2 to enable the surgeon to use another voltage than actually delivered by the bipolar electrosurgical generator 2 to the loop electrode 12.

As seen in FIG. 2a the transformer 9 has a core 19 (e.g. a laminated core, an iron core, a ferrite core or the core can consist of air) presenting a first section 20, the input side or input end, with the primary coil 8, and a second section 21, the output side or output end, with the secondary coil 11. The primary coil 8 has a first number NP of primary windings 22, and the secondary coil 11 has a second number NS of secondary windings 23, which second number NS are larger than the first number NP. In the case shown the second number NS is an example double the first number NP but less and more numbers are possible and intended within the scope of the present invention.

If the bipolar electrosurgical generator 2 provides an electric current to the bipolar electrosurgical instrument 1, an electric current will flow via electric wire B1 through the primary windings 22. The current through the primary windings 22 will induce a magnetic field through the primary coil 8. The magnetic field from the primary coil is enhanced by the core 19 and transferred to the secondary coil 11. The magnetic field through the secondary coil will induce a current in the secondary windings 23. The current goes in preferably the following order: via the electric conductor B21 through the loop electrode 12 to the tip 12b over to an object (not shown), one or more of the four flat conductive plates or blades 16a,16b,16c,16d, the corresponding electric electrode wires 14a,14b and the electric conductor B22 back to the secondary windings 23.

In an ideal voltage transformer a secondary voltage Vs induced in the secondary windings 23 is in proportion to a primary voltage Vp in the primary windings 22, and is given by the ratio between the first number of windings NP and the second number of windings NS:

The core 19 with primary coil 8 and secondary coil 11 respectively, as shown in FIG. 1, is as mentioned configured to be incorporated in the tubular handle 13, or any other longitudinal part of the electrosurgical instrument 1 suited for accommodating said transformer 9, which first handle 13 or other suitable part fits the palm of the hand of the surgeon.

It is of course to be understood that the transformer according to the present invention can have any kind and length and number of windings that provides a bipolar electrosurgical instrument that complies with various national standards and surgical conditions.

A typical bipolar electrosurgical generator for use in the present invention transmits high-frequency (HF) energy ranging from 350 KHz to 1 MHz. The transformer is inserted between the bipolar electrosurgical generator 2 and the instrument 1 to increase voltage.

In an exemplary embodiment a step-up transformer 9 having twice as many secondary windings 23 at the secondary coil 11 than primary windings 22 at the primary coil 8 is connected to a 357 kHz bipolar electrosurgical generator 2. Double voltage and fourfold power are the beneficial results. This bipolar electrosurgical arrangement of the above bipolar electrosurgical generator and bipolar electrosurgical instrument with transformer is able to deliver 200 W for 20 seconds.

When an object (not shown) is situated between and in electrical contact with the electrodes, which means in electrical contact with the spread apart four flat conductive plates or blades 16a,16b,16c,16d and also in electrical contact with the tip 12b of the loop electrode 12, it is possible to establish a value of the impedance, resistance or capacity to be used as an indication of the presence of an object to inform the surgeon that cutting or coagulating current can be switched on, or off if no contact is established, or that voltage needs amplification.

Figure 2B:
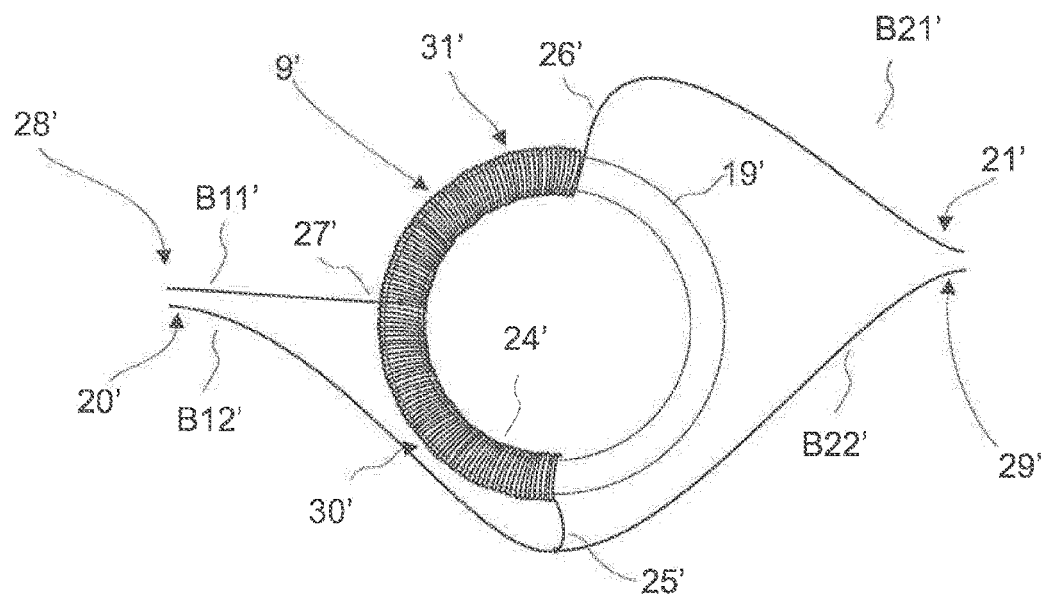
FIGS. 2b and 2c illustrate in an enlarged scale, the transformer of the bipolar electrosurgical loop instrument shown in FIG. 1, where the transformer is an autotransformer with a primary side and a secondary side.
Figure 2C:
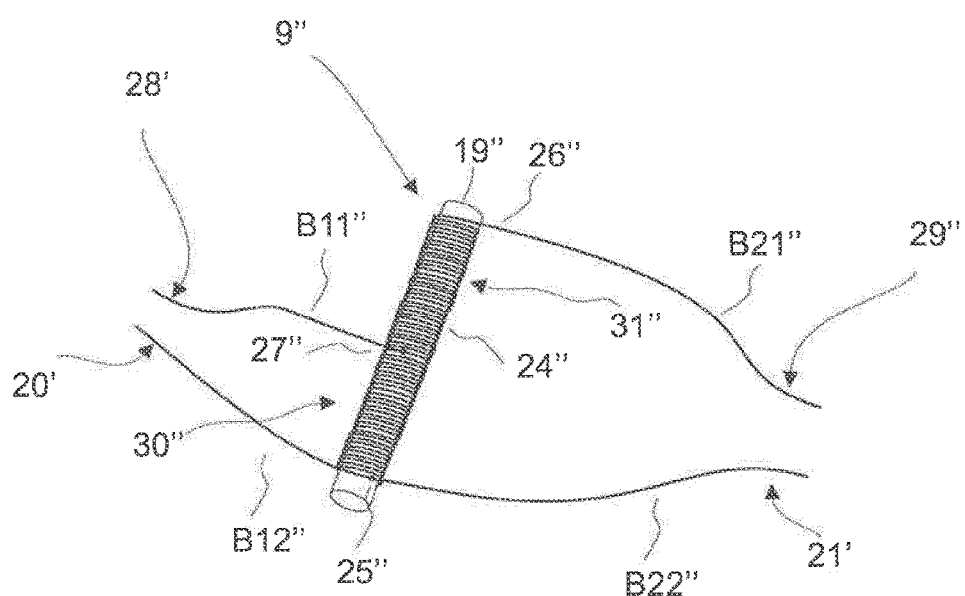

FIGS. 2b and 2c show a second and a third embodiment of a transformer 9';9" that correspond substantially to the transformer 9, and for like parts same reference numerals are used.

The transformers 9' and 9" are autotransformers, where the transformer in FIG. 2b is a toroidal transformer 9' and the transformer in FIG. 2c is a bar-type transformer 9".

The toroidal autotransformers 9' and the bar-type autotransformers 9" comprise an input side or input end 20';20" and an output side or output end 21';21".

The toroidal autotransformer 9' or the bar-type autotransformer 9" has one coil 24';24" surrounding the core 19';19" (e.g. a ferrite core) between a first terminal 25';25" and a second terminal 26';26". A third terminal 27';27" is connected to the coil 24';24" between the first terminal 25';25" and the second terminal 26';26". The electric conductors B11';B11" and B12';B12" from the bipolar electrosurgical generator 2 are connected to the third terminal 27';27" and the first terminal 25';25", respectively, while the electric conductors B21';B21" and B22';B22" are connected to the second terminal 26';26" and the first terminal 25';25", respectively. Since there is only one coil, both the primary side 28';28" and the secondary side 29';29" have a first part of the coil 30';30" between the first terminal 25';25" and the third terminal 27';27" in common.

Since the transformer is used to amplify the voltage, the secondary side of the transformer comprises also a further second part of the coil 31';31" between the third terminal 27';27" and the second terminal 26';26". The first part of the coil 30';30" is the primary coil. The first part of the coil 30';30" and the second part of the coil 31';31" which is the whole coil 24';24" is the secondary coil.

Since in an autotransformer some of the coil is used for both the primary side and the secondary side the autotransformer can be made lighter, smaller and cheaper compared to a transformer with two separate windings. The toroidal autotransformer can be made with a diameter that is small enough that the toroidal autotransformer can fit inside the handle 13 of the bipolar electrosurgical loop instrument 1.

Figure 3A:
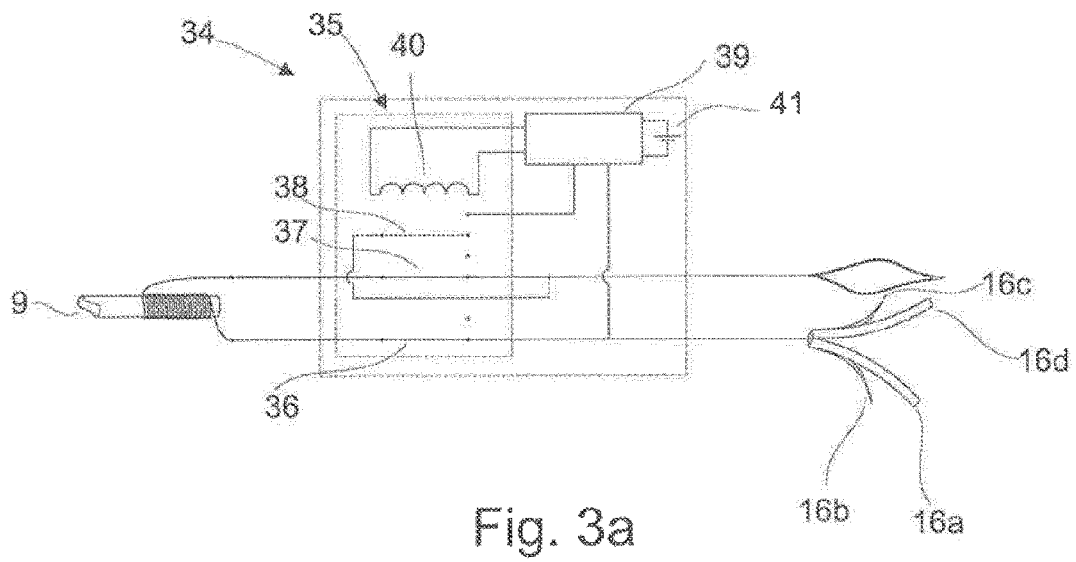
FIG. 3a illustrates, the timer/measurement unit controlling the switches, where the switches are relays and where the switches are positioned so that the instrument is in the operating mode so that the power from the generator is provided to the electrodes.
Figure 3B:
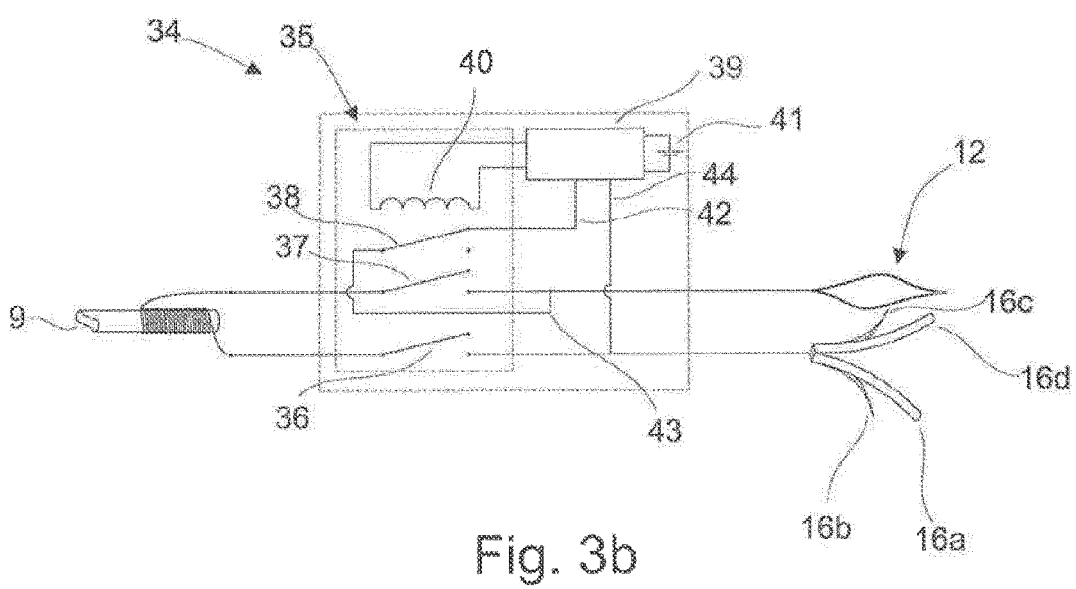
FIG. 3b illustrates, the timer/measurement unit controlling the switches, where the switches are relays and where the switches are positioned so that the instrument is in the measurement mode so that the timer/measurement unit is connected to the electrodes and is able to measure the impedance between the electrodes.

FIGS. 3a and 3b are schematic drawings of the circuit 34, where the switches are relays. FIG. 3a shows the circuit 34 when the bipolar electrosurgical instrument 1 is in the operating mode, and FIG. 3b shows the circuit when the bipolar electrosurgical instrument is in the measurement mode. In FIGS. 3a and 3b the transformer 9 is for illustrative purposes shown fragmented by fragment lines 9a.

A relay 35 is placed in the electric wire B2 between the transformer 9 on one hand, and the electrodes like e.g. the loop electrode 12 and the flat conductive plates or blades 16a,16b,16c,16d on the other hand. The relay 35 controls switches 36,37 between the transformer and the electrodes as well as a switch 38. The relay is controlled by a timer/measurement unit 39 through e.g. an electromagnet 40. The timer/measurement unit 39 might have a battery 41 to be able to operate, or are supplied by the bipolar electrosurgical generator 2, e.g. by a low voltage output (not shown) or by the output B. All three switches 36,37,38 are changed simultaneously to go from operation mode to measurement mode and back again in a recurring cycle The cycle is less than 5 sec. long, preferably less than 1 sec. long, more preferably less than 300 msec. long, even more preferably less than 100 msec. long, yet more preferably less than 30 msec. long, yet even more preferably less than 10 msec. long, further more preferably less than 3 msec. long, even further more preferably less than 1 msec. long, yet further more preferably less than 300 μsec. long, yet even further more preferably less than 100 μsec. long and most preferably less than 30 μsec. long.

When the switches 36,37 are closed the switch 38 is opened and vice versa. In the operation mode, which is e.g. 9/10 of the cycle the switches 36,37 are closed and the switch 38 is open. In the operation mode the bipolar electrosurgical generator will preferably drive current in the following order: via the transformer and the switches 36,37 through the loop electrode 12, an object (not shown) and the flat conductive plates or blades 16a,16b,16c,16d. When the 9/10 of the cycle has elapsed the timer/measurement unit 39 switches the relay to the measurement mode by opening the switches 36,37 and closing the switch 38. In the measurement mode the timer/measurement unit 39 is connected to the electrodes, like e.g. the loop electrode 12 and the flat conductive plates or blades 16a,16b,16c,16d via electrical conductors 42,43 and switch 38 as well as electrical conductor 44. By applying a voltage over the loop electrode 12 and the flat conductive plates or blades 16a,16b,16c,16d and measuring the current through the loop electrode 12, the object (not shown) as well as the flat conductive plates or blades 16a,16b,16c,16d, the timer/measurement unit 39 has means to calculate the impedance of the object. The bipolar electrosurgical instrument has means to calculate the current needed to easily and effectively cut the tissue or coagulate the tissue and avoid driving so much current through the tissue that the tissue will burn and create a lot of smoke. If the calculated impedance is infinite there might be no switch over to the operation mode.

The relay could also be placed between the bipolar electrosurgical generator and the transformer.

Conventional bipolar electrosurgical generators are often unable to deliver a sufficient high voltage to enable fast cutting or coagulation of tissue thereby prolonging surgical intervention unnecessary long.

Bipolar electrosurgical instruments in the form of forceps or tweezers have opposite poles, i.e. electrodes that clamp around the tissue while coagulation is performed. In order to perform well the electrodes must from time to time during the surgery be cleaned to remove inter alia clots and burned tissues or other kinds of tissue residues that eventually deposit on the electrode surfaces and/or be greased to avoid fast deposition of the aforementioned undesired components.

Some bipolar electrodes have a Teflon™ coating to minimize disadvantageous tendency of tissue residue depositing. The low voltage applied by the bipolar electrosurgical generator to the opposite facing electrodes is insufficient to overcome the impedance of even a thin Teflon™ coating or other similar heat resistant coating. The present invention proposes a simple means to amplify voltage applied by conventional bipolar electrosurgical generator when using bipolar electrosurgical instruments, in particular bipolar electrosurgical instruments with heat resistant coatings.

Figure 4A:
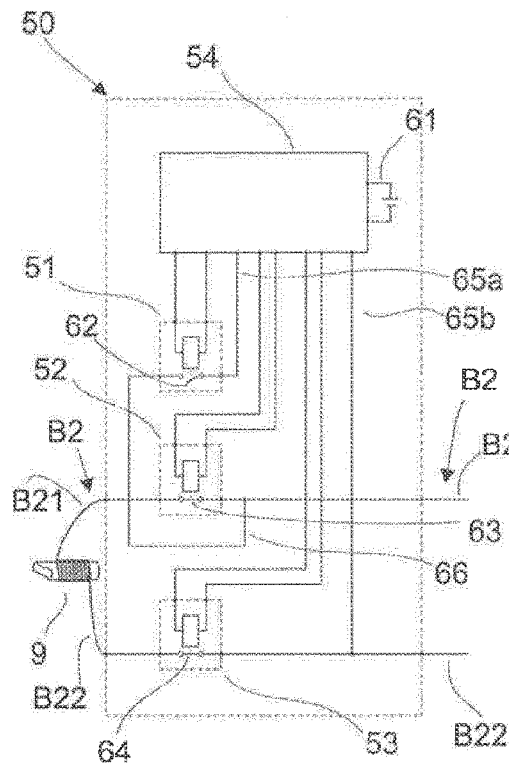
FIGS. 4a-d illustrate the timer/measurement unit controlling the switches, where the circuit is built up by semiconductors.
Figure 4B:
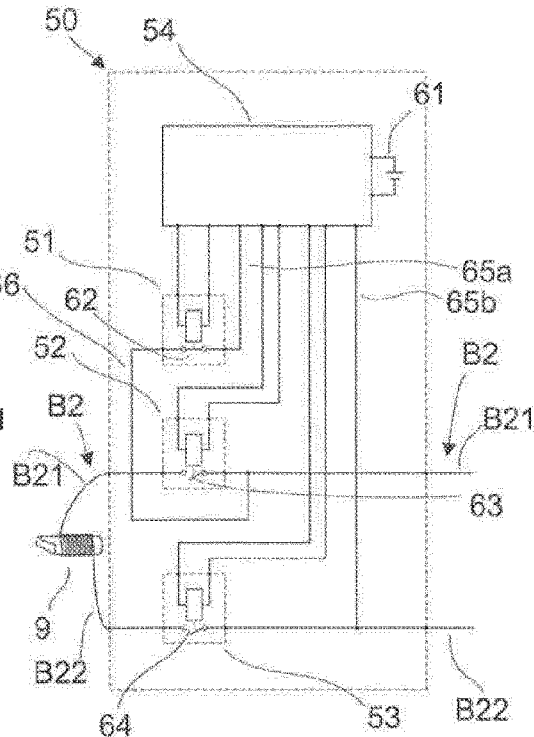

FIGS. 4a and 4b disclose like in FIGS. 3a and 3b a circuit 50 placed between the transformer 9 on one hand, and the electrodes like e.g. the loop electrode 12 and the flat conductive plates or blades 16a,16b,16c,16d on the other hand. The circuit 50 in FIGS. 4a and 4b have all the properties as the circuit 9 in FIGS. 3a and 3b and can be described in exactly the same manner as the circuit 9 in FIGS. 3a and 3b, except that the relays in circuit 50 are electronic relays 51,52,53. A timer/measurement unit 54 controls the electronic relays. The timer/measurement unit 54 can be driven by a battery 61, by the bipolar electrosurgical generator 2 or by any other power supply. The timer/measurement unit 54 in the operation mode shown in FIG. 4a controls the electronic relay 51 to keep a switch 62 open and controls the electronic relays 52 and 53 to keep switches 63 and 64 closed so that the bipolar electrosurgical generator 2 is able to drive a cutting or coagulating current in preferably the following order: through the loop electrode 12, the object (not shown) and the four flat conductive plates or blades 16a,16b,16c,16d.

In the measurement mode, shown in FIG. 4b, the timer/measurement unit 54 controls the electronic relays 51,52,53 to keep the switches 62,63,64 in a position opposite to the position in the operation mode. In the measurement mode, the timer/measurement unit 54 is connected via an electrical conductor 65a to an electrical conductor 66 by the electronic relay 51, and further to the electric conductors B21 and the loop electrode 12. The timer/measurement unit 54 is also connected via an electrical conductor 65b to electric conductor B22 and the flat conductive plates or blades 16a,16b, 16c,16d. In the measurement mode, the timer/measurement unit 54 has means to apply a voltage over the loop electrode 12 and the flat conductive plates or blades 16a,16b,16c,16d, measure the current through the object (not shown) between the loop electrode 12 and the flat conductive plates or blades 16a,16b,16c,16d and calculate the impedance of the object.

All three switches 62,63,64 are changed simultaneously to go from operation mode to measurement mode and back again in a recurring cycle.

Figure 4C:
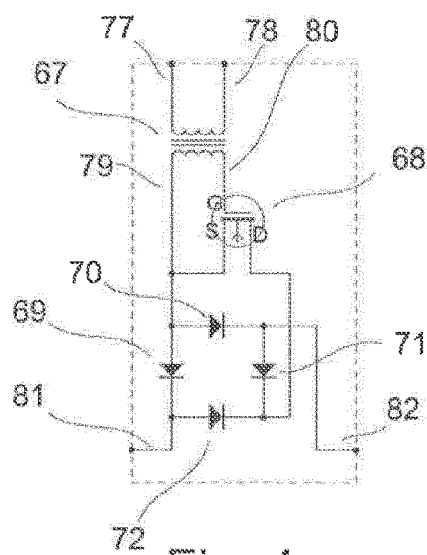
Figure 4D:
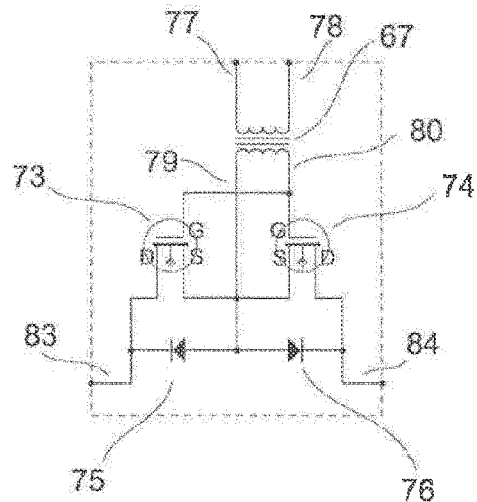

In FIGS. 4c and 4d two different embodiments of the electronic relays 51,52,53 are disclosed. The electronic relay in FIG. 4c comprises a pulse transformer 67, a MOSFET transistor 68, and four diodes 69,70,71,72. In FIG. 4d the electronic relay comprises the pulse transformer 67, two MOSFET transistors 73,74 and two diodes 75,76.

A control voltage in form of a pulse is applied by the timer/measurement unit 54, via electrical conductors 77,78 over the pulse transformer 67. The control voltage over the electrical conductors 77,78 is transferred by the pulse transformer and applied on the electrical conductors 79,80 as a terminal voltage. The transformer 67 can amplify the signal from the timer/measurement unit 54 to the electrical conductors 79,80 but the transformer can also be a 1:1-transformer. The object of the transformer 67 is to isolate the control voltage from the terminal voltage, so that the control voltage and the terminal voltage can be at different potentials without disturbing or interfering with the electronics in the timer/measurement unit 54. The terminal voltage will be applied over the gate G and the source S (VGS) of the MOSFET transistor 68 in FIG. 4c and of the two MOSFET transistors 73,74 in FIG. 4d. The terminal voltage exceeds the threshold voltage (VGS>VTH) of the one or more MOSFET transistors and opens for current to flow between the drain D and the source S of the one or two MOSFET transistors.

The pulse transformer 67 is designed to keep the positive charge at the gate long enough to keep the one or two MOSFET transistors 73,74 open until the circuit 50 changes from operation mode to measurement mode and vice versa.

To close or block the one or two MOSFET transistors and stop current to flow from the drain D to the source S a pulse with a negative potential is sent to the pulse transformer 67 by the timer/measurement unit 54. The pulse with the negative potential is transferred by the pulse transformer and applied over the gate G and the source S so that VGS<VTH.

If VGS>VTH of the MOSFET transistor 68 in FIG. 4c is true, the bipolar electrosurgical generator 2 can drive current going into the electronic relay at an electrical conductor 81, through diode 72, through the MOSFET transistor 68 from the drain to the source, through the diode 70 and out through an electrical conductor 82 and further to the object. The bipolar electrosurgical generator 2 can also drive the current in through the electrical conductor 82, the through the diode 71, through the MOSFET transistor 68 from the drain to the source, through the diode 69 and out through the electrical conductor 81 back to the bipolar electrosurgical generator 2. Likewise, the electronic relay in FIG. 4c can, when the electrical conductor 81 is connected to the electrical conductor 65a from the timer/measurement unit 54, be used to allow or to block the timer/measurement unit 54 to drive current in the following order: from the electrical conductor 65a through the electrical conductors 81,82, further via electrical conductors 66, the loop electrode 12, the object and back through the flat conductive plates or blades 16a, 16b,16c,16d and the electrical conductor 65b to the timer/measurement unit 54.

In FIG. 4d an electrical conductor 83 will connect to the bipolar electrosurgical generator 2 or to the electrical conductor 65a from the timer/measurement unit 54. When the terminal voltage is applied over the gate G and the source S of the two MOSFET transistors 73,74 current entering through electrical conductor 83 will pass the MOSFET transistor 73 from drain D to source S and through the diode 76 and out through an electrical conductor 84, while a current entering through the electrical conductor 84 will pass the MOSFET transistor 74 from drain D to source S and through the diode 75 and out through the electrical conductor 83.

The advantage of using the semi-conductor based circuit instead of the circuit 9 disclosed in FIGS. 3a and 3b is that the semi-conductor based circuit will be able to shift much faster between the operation mode and the measurement mode. With the semi-conductor based circuit it will be possible to shift between the operation mode and the measurement mode and back again in milliseconds and even in microseconds.

Instead of using MOSFET transistors other FET transistors can be used like e.g. IGBT. The channel of the FET can either be doped to produce an N-type semiconductor or a P-type semiconductor. The transistors can also be NPN-transistors or PNP-transistors or the circuit can be made of any kind of semiconductor. Likewise the pulse transformer to control the one or more transistors can also be an Optomos®, any kind of optical relay or any kind of gate driver circuit. The person skilled in the art will know how to design modifications of such a semi-conductor based circuit and such an optical relay or gate driver circuit. Such modifications are also intended within the scope of the present invention.

Figure 5:
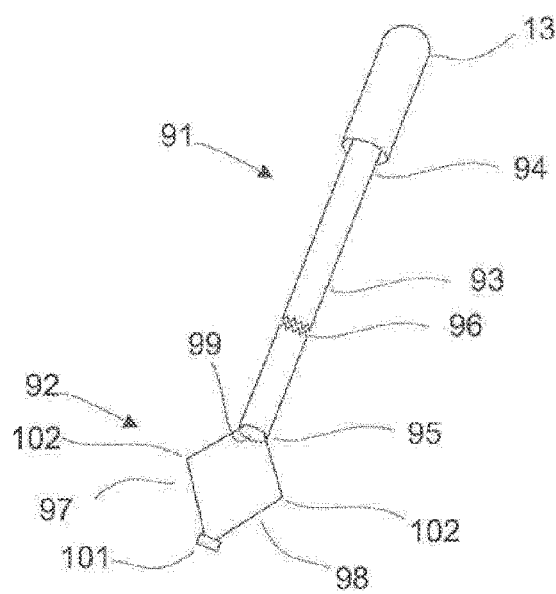
FIG. 5 illustrates, a schematic view of a bipolar electrosurgical loop instrument with an alternative loop electrode.

In FIG. 5 a sketch of a second bipolar electrosurgical instrument 91 is for illustrative purposes shown fragmented by fragment lines 96. The second bipolar electrosurgical instrument 91 has all the features of the bipolar electrosurgical instrument 1 as described above. The only difference is how the electrodes 92 are elaborated. Like the bipolar electrosurgical instrument 1 the second bipolar electrosurgical instrument 91 has a hollow shaft 93 with a proximal end 94 and a distal end 95.

The electrodes of the second bipolar electrosurgical instrument 91 comprise two metal wire parts 97,98 that protrude from a first opening 99 in the distal end 95. The two metal wire parts 97,98 are connected to the two electric conductors B21 and B22 from the transformer 9. To avoid the two metal wire parts 97,98 to touch each other and cause a short-circuit the distal end of the two metal wire parts 97,98 are moulded into a holding member 101, where the two metal wire parts 97,98 are not contacting each other. The holding member 101 is made of an insulating material. The advantage of this embodiment is that the two metal wire parts 97,98 will never contact each other and cause a short-circuit.

The two metal wire parts 97,98 have both a knee 102 so that the two metal wire parts 97,98 are bent away from each other to avoid contacting each other and to allow an easy access of the tissue to be cut off between the two metal wire parts 97,98.

Figure 6A:
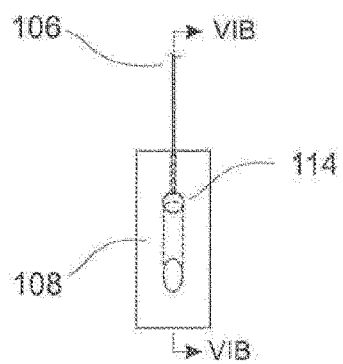
FIGS. 6a and b illustrate the holding member and how the holding member connects the ends of the metal wire parts of the loop electrode.
Figure 6B:
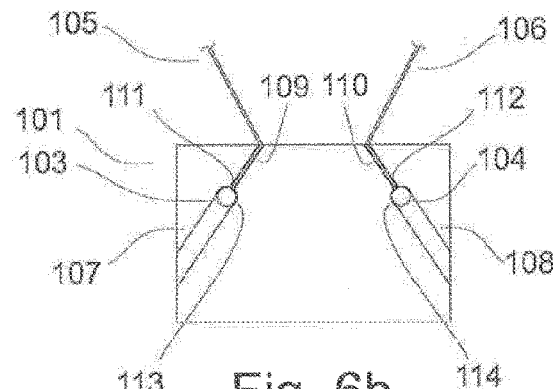
Figure 7A:
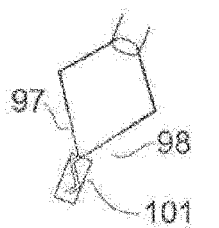
FIGS. 7a-d illustrate further alternative loop electrodes.
Figure 7B:
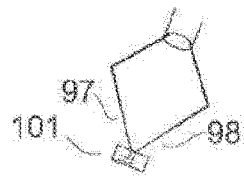
Figure 7C:
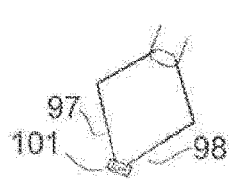
Figure 7D:
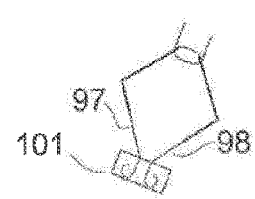

To have the ends of the two metal wire parts 97,98 to stay in the holding member 101, the ends of the two metal wire parts 97,98 have each their knot 103,104 at the ends of the two metal wire parts that are in the holding member 101, as indicated in FIGS. 6*a* and 6*b*.

FIG. 6*b* shows a sectional view taken along line VIb-VIb in FIG. 6*a* of the holding member 101 to illustrate the interior components of said holding member. First and second wire parts 105,106 with first and a second ends, where the first end has the knot 103,104 are introduced into and through a first channel 107,108 and then through a second channel 109,110 with the second end first. Since the diameter of the knot is smaller than or equally big as the first channel 107,108 and is bigger than the second channel 109,110 the knot will be caught at a second opening 111,112 of the second channel 109,110. When the first and second metal wire parts are introduced so far that the knot is pressed against the second opening 111,112 of the second channel 109,110 the first and second metal wire parts 105,106 are bent manually just outside the holding member 101. In that way the first and second metal wire parts are fixed. Where the first channel meets the second channel the first channel can have an increased diameter like a spherical cavity 113,114. The advantage of the spherical cavity is that the knot will be prevented to fall back through the first channel 107,108. The knot can be made of an elastic material and the first channel can be made just a little smaller than the diameter of the knot so that the knot has to be squeezed when pulled through the first channel. The ends of the first and second metal wire parts 105,106 sticking out of the holding member 101 are welded or in any other way attached to the two metal wire parts 97,98 or to the two electric conductors B21 and B22. In FIGS. 6*a* and 6*b* the first and second wire parts 105,106 is for illustrative purposes shown fragmented by fragment lines 100.

The two metal wire parts 97,98 can also be bent as shown in FIGS. 7*a-d*. The advantage is here that the first and second metal wire parts 105,106 do not need to be welded or in any other way attached to the metal wire parts 97,98. The metal wire parts can just be moulded or glued into the holding member 101.

It is to be understood that within the scope of the present invention the features, such as transformer and various circuits, can be combined as desired and feasible, into embodiments and modified instruments not shown in the figures. Thus the embodiments shown in said figures should not be construed as limiting the scope of the present invention: E.g. the embodiment of an electrosurgical instrument 1, shown in FIG. 1, may also comprise any of the circuits shown in FIGS. 3*a*-3*b* and 4*a*-4*d*. Also any of the embodiments of an electrosurgical instrument 91 shown in FIGS. 5, 6*a*, 6*b* and 7*a*-7*d* may include the transformer 9;9';9".

The present invention proposes an inexpensive bipolar electrosurgical instrument for use with most conventional bipolar electrosurgical generators as well as with bipolar electrosurgical generators specifically designed for use with said instrument.

The invention claimed is:
1. A method of electrically powering different handheld electrosurgical cutting instruments which require different voltage, the method comprising:
    providing a single electrosurgical generator;
    providing at least two different handheld electrosurgical instruments each having electrodes for cutting or cauterization and requiring different voltage from the electrosurgical generator,
    characterized in that both electrosurgical instruments are connected to receive identical electrical signals from the electrosurgical generator, and
    the electrical signal for at least one of the handheld electrosurgical instruments is changed by use of a transformer connected between the electrosurgical generator and the electrodes of one of the electrosurgical instruments.

* * * * *